United States Patent [19]

Gosch et al.

[11] Patent Number: 4,990,692

[45] Date of Patent: Feb. 5, 1991

[54] REMOVAL OF CYCLOHEXANOL

[75] Inventors: Hans-Juergen Gosch, Bad Duerkheim; Rolf Fischer, Heidelberg, both of Fed. Rep. of Germany

[73] Assignee: BASF Aktiengesellschaft, Ludwigshafen, Fed. Rep. of Germany

[21] Appl. No.: 383,058

[22] Filed: Jul. 21, 1989

[30] Foreign Application Priority Data

Aug. 27, 1988 [DE] Fed. Rep. of Germany ....... 3829143

[51] Int. Cl.$^5$ .................. C07C 29/04; C07C 29/74
[52] U.S. Cl. .................. 568/835; 568/810;
568/834; 568/868; 568/895; 568/899
[58] Field of Search ............ 568/835, 810, 834, 868, 568/895, 899

[56] References Cited

U.S. PATENT DOCUMENTS

| | | | |
|---|---|---|---|
| 2,927,944 | 3/1960 | Giesen et al. | 568/835 |
| 2,974,174 | 3/1961 | Edmoston | 568/835 |
| 4,306,101 | 12/1981 | Slaugh et al. | 568/835 |
| 4,691,064 | 9/1987 | Shirafuji et al. | 568/835 |

FOREIGN PATENT DOCUMENTS

| | | | |
|---|---|---|---|
| 0123713 | 11/1984 | European Pat. Off. | 568/835 |
| 227931 | 11/1986 | European Pat. Off. | 568/835 X |
| 0285911 | 10/1988 | European Pat. Off. | 568/835 |
| 2103033 | 5/1987 | Japan | 568/835 |

Primary Examiner—Werren B. Lone
Attorney, Agent, or Firm—Keil & Weinkauf

[57] ABSTRACT

Cyclohexanol is removed from aqueous solutions containing it and aromatic sulfonic acids by extraction with one or more cyclohexyl ethers liquid under extraction conditions and having the formula

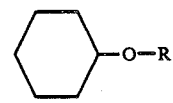

I where R is alkyl of from 1 to 16 catbon atoms, cycloalkyl of from 5 to 8 carbon atoms, aralkyl of from 7 to 10 carbon atoms or phenyl, which may additionally have substituents which are inert under reaction conditions.

6 Claims, No Drawings

REMOVAL OF CYCLOHEXANOL

European Patent Application 123,713 discloses a process wherein cyclohexanol is obtained by hydrating cyclohexene at from 50° to 200° C. in from 5 to 80% strength by weight solutions of aromatic sulfonic acids in water. To prevent corrosion, the reaction is carried out for example in the presence of heteropoly acids, salts or oxides of molybdenum, tungsten or vanadium. The cyclohexanol formed by hydration of cyclohexene predominantly dissolves in the aqueous phase, which contains the aromatic sulfonic acid, and is mostly not removed therefrom even by excess cyclohexene.

JP-A2-103,033/1987 recommends aliphatic, cycloaliphatic and aromatic hydrocarbons for extracting cyclohexanol from aqueous solutions of aromatic sulfonic acids. However, appreciable amounts of extractants are necessary to obtain effective extraction, Industrially, this is very expensive.

In a process described in European Patent Application 227,931, the hydration of cyclohexene is carried out in aqueous solutions of aromatic sulfonic acids with one or more hydroxyl groups on the aromatic ring and the cyclohexanol is subsequently extracted with aromatic hydrocarbons. It is true that with this process it is possible to reduce the amount of extractant, but the use of hydroxyl-containing aromatic sulfonic acids substantially reduces the yield of and selectivity for cyclohexanol.

It is an object of the present invention to improve the removal of cyclohexanol from aqueous aromatic sulfonic acid solutions as obtained in the hydration of cyclohexene in the presence of aromatic sulfonic acids.

We have found that this object is achieved by a process for removing cyclohexanol from aqueous solutions containing it and aromatic sulfonic acids by extraction using as the extractant a cyclohexyl ether liquid under extraction conditions and having the formula

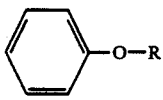   I where R is alkyl of from 1 to 16 carbon atoms, cycloalkyl of from 5 to 8 carbon atoms, aralkyl of from 7 to 10 carbon atoms or phenyl, which may each additionally have substituents which are inert under reaction conditions.

The novel process has the advantage that the amount of extractant to be used is appreciably reduced and a better extraction result is obtained. This is even true if hydroxyl-free sulfonic acids are used as hydrating agents in the preparation of cyclohexanol, which additionally increases the yield of cyclohexanol.

According to the invention, the starting point is an aqueous solution which contains cyclohexanol and an aromatic sulfonic acid in solution. A solution of this type is obtained in the hydration of cyclohexene to cyclohexanol by reacting cyclohexene in an aqueous solution which contains from 5 to 80% by weight of an aromatic sulfonic acid, in particular a benzene- or naphthalene-sulfonic acid, which may be substituted, such as benzenesulfonic acid, toluenesulfonic acid or naphthalenesulfonic acid, or dodecylbenzenesulfonic acid, at from 50° to 200° C., in particular from 70° to 150° C., under from 1 to 10 bar. It is advantageous to use in addition molybdenic acid or a salt thereof, vanadium oxide or a vanadate in an amount of for example from 0.001 to 5% by weight, based on the aromatic sulfonic acid. In addition, it is also advisable to use a heteropoly acid such as phosphorusmolybdenic acid, phosphorustungstic acid, phosphorusmolybdenictungstic acid or phosphorusmolybdenicvanadic acid. Suitable processes are described for example in European Patent No. 123,713 and European Patent Application 206,631. The resulting reaction mixture separates into an organic phase comprising excess cyclohexene, which contains minor amounts of cyclohexanol. The aqueous phase obtained is typically composed for example of from 5 to 10% by weight of cyclohexanol, from 40 to 70% by weight of aromatic sulfonic acids and from 20 to 50% by weight of water. The cyclohexene phase can be separated off, by example by decanting, and worked up separately. However, it is not absolutely necessary to separate off the cyclohexene before the extraction since it can be utilized as an additional extractant.

According to the invention, the aqueous solutions containing cyclohexanol and aromatic sulfonic acids are extracted with one or more cyclohexyl ethers of the formula I where R is alkyl of from 1 to 16 carbon atoms, cycloalkyl of from 5 to 8 carbon atoms, aralkyl of from 7 to 10 carbon atoms or phenyl, which may each have substituents which are inert under the reaction conditions. The cyclohexyl ethers of the formula I used as extractants should be liquid under extraction conditions. It will be readily understood that they are substantially or completely water-immiscible. The radicals R may contain for example up to two inert substituents such as chlorine atoms or alkoxy groups. Preferably, the radical R has a hydrocarbon structure.

Suitable ethers are for example cyclohexyl benzyl ethers, cyclohexyl alkyl ethers and cyclohexyl aryl ethers. It is particularly advantageous to use cyclohexyl ethers such as cyclohexyl methyl ether, cyclohexyl ethyl ether, cyclohexyl n-propyl ether, cyclohexyl i-propyl ether, cyclohexyl n-butyl ether, cyclohexyl i-butyl ether or phenyl cyclohexyl ether.

In preferred cyclohexyl ethers of the formula I, R is alkyl of from 1 to 12 carbon atoms or cyclohexyl. Dicyclohexyl ether has become particularly important.

For every part by volume of the aqueous solution of aromatic sulfonic acid and cyclohexanol to be extracted it is advantageous to use from 0.1 to 50 parts by volume, in particular from 1 to 10 parts by volume, of extractant. The extraction in general is carried out at from 0 to 200° C., advantageously from 10° to 100° C., in particular from 10° to 50° C.

The extraction of the aqueous solution containing cyclohexanol and aromatic sulfonic acid can be carried out batchwise by mixing the aqueous solution intensively with the extractant and subsequently separating the phases. Advantageously, the extraction is carried out continuously in countercurrent in suitable extraction columns such as stirred disk columns, pulsed columns or single- or multi-stage mixer settlers. The aqueous phase obtained, which contains aromatic sulfonic acids, is reused for the hydration of cyclohexene, while the cyclohexanol-containing extractant phase is worked up by distillation. If small amounts of aromatic sulfonic acids end up in the cyclohexanol-containing extract, they are easily removable by washing with a little water and are advantageously added to the aqueous hydrating solution.

Particularly advantageously, the cyclohexyl ethers I used as extractants have a higher boiling point than cyclohexanol. As a consequence, it is only necessary to separate the cyclohexanol from the extractant by distillation. The extractant obtained as the bottom phase is advantageously recycled into the extraction stage. In a preferred embodiment, the extraction is carried out using the excess cyclohexene phase obtained in the hydration. The subsequent workup thus gives first a cyclohexene fraction, which is reused for the hydration, a cyclohexanol fraction and, as the bottom product, the extractant.

The cyclohexanol obtainable by the process of the invention is suitable for preparing cyclohexanone, an important starting material for caprolactam.

The process according to the invention is illustrated by the Examples below. The parts by weight bear the same relation to parts by volume as the kilogram to the liter.

EXAMPLE 1

17.4 parts by volume of an aqueous solution of 54% parts by weight of p-toluenesulfonic acid, 10% parts by weight of cyclohexanol and 36% parts by weight of water were intensively mixed with 21.5 parts by volume of dicyclohexyl ether in a vessel at room temperature for 5 minutes. After phase separation it was found by gas chromatography that 19.4% by weight of the cyclohexanol used had been extracted from the aqueous phase.

COMPARATIVE EXAMPLES 1–5

The extraction was carried out as described in Example 1, except that in each case the hydrocarbons indicated in the table were used for the extraction. The results are shown in the table:

TABLE

| Comparative Example | Extractant | Extracted cyclohexanol [% by weight] |
|---|---|---|
| 1 | cyclohexene | 13.7 |
| 2 | toluene | 16.4 |
| 3 | tetralin | 14.4 |
| 4 | decalin | 5.2 |
| 5 | 4-tert-butyltoluene | 11.6 |

We claim:

1. A process for removing cyclohexanol from an aqueous solution containing it and an aromatic sulfonic acid by extraction with one or more cyclohexyl ethers liquid under extraction conditions and having the formula

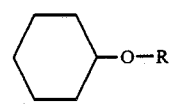

where R is alkyl of from 1 to 16 carbon atoms, cycloalkyl of from 5 to 8 carbon atoms, aralkyl of from 7 to 10 carbon atoms or phenyl, which may each additionally have substituents which are inert under the reaction conditions.

2. A process as claimed in claim 1, wherein a cyclohexyl ether of the formula I where R is alkyl of from 1 to 12 carbon atoms or cyclohexyl is used.

3. A process as claimed in claim 1, wherein dicyclohexyl ether is used.

4. A process as claimed in claim 1, wherein from 1 to 10 parts by volume of extractant of the formula I are used per part by volume of aqueous solution.

5. A process as claimed in claim 1, wherein the extraction is carried out at from 10° to 100° C.

6. A process as claimed in claim 1, wherein an aqueous solution obtained by hydration of cyclohexene in an aqueous solution of an aromatic sulfonic acid is used for the extraction without removal of the excess cyclohexene.

* * * * *